United States Patent
Van Hal et al.

(10) Patent No.: US 9,795,443 B2
(45) Date of Patent: Oct. 24, 2017

(54) HAIR-GROWTH CONTROL DEVICE AND HAIR-GROWTH CONTROL METHOD

(75) Inventors: Robbert Adrianus Maria Van Hal, Eindhoven (NL); Rieko Verhagen, Eindhoven (NL); Guido Roosen, Eindhoven (NL); Michiel Errit Roersma, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1821 days.

(21) Appl. No.: 11/914,154

(22) PCT Filed: May 8, 2006

(86) PCT No.: PCT/IB2006/051438
§ 371 (c)(1),
(2), (4) Date: Nov. 12, 2007

(87) PCT Pub. No.: WO2006/120635
PCT Pub. Date: Nov. 16, 2006

(65) Prior Publication Data
US 2008/0228178 A1    Sep. 18, 2008

(30) Foreign Application Priority Data

May 12, 2005  (EP) .................................... 05103975
May 8, 2006   (WO) ................. PCT/IB2006/051438

(51) Int. Cl.
*A61B 18/20* (2006.01)
*A61B 18/00* (2006.01)

(52) U.S. Cl.
CPC ............ *A61B 18/203* (2013.01); *A61B 18/20* (2013.01); *A61B 2018/00452* (2013.01); *A61B 2018/00476* (2013.01); *A61B 2018/00904* (2013.01)

(58) Field of Classification Search
CPC ...................................................... A61B 18/20
See application file for complete search history.

(56) References Cited

U.S. PATENT DOCUMENTS 3,538,919 A    11/1970 Meyer
3,693,623 A *  9/1972 Harte et al. ...................... 606/9
(Continued)

FOREIGN PATENT DOCUMENTS

DE     10013910    10/2001
FR      2590791     6/1987
(Continued)

OTHER PUBLICATIONS

El Gammal: "Sonography of the Skin at 100 MHz Enables In Vivo Visualization of Stratum Corneum and Viable Epidermis in Palmar Skin and Psoriatic Plaques", vol. 113, NR 5, 821-829 (1999).

*Primary Examiner* — Lynsey Crandall

(57) ABSTRACT

The invention relates to a device (1) for hair-growth control of hairs (3), in particular hairs growing from human skin (5). The device (1) has a laser source (7) for generating a laser beam (9) during a pulse time, an optical system (15) for focusing the laser beam into a focal spot (25), and a laser beam manipulator (17) for positioning the focal spot in a target position. According to the invention, a dimension of the focal spot (25) and a power of the generated laser beam (9) are such that, in the focal spot (25), the laser beam has a power density which is above a characteristic threshold value for hair-growth related skin tissue above which, for the pulse time, a laser induced optical breakdown (LIOB) phenomenon occurs in the hair-growth related skin tissue. The LIOB phenomenon results in a number of mechanical effects, such as cavitation and the generation of shock waves, which damage the hair-growth related skin tissue in positions surrounding the LIOB phenomenon. An advantage of the device (1) according to the invention is that the (Continued)

Figure 1:
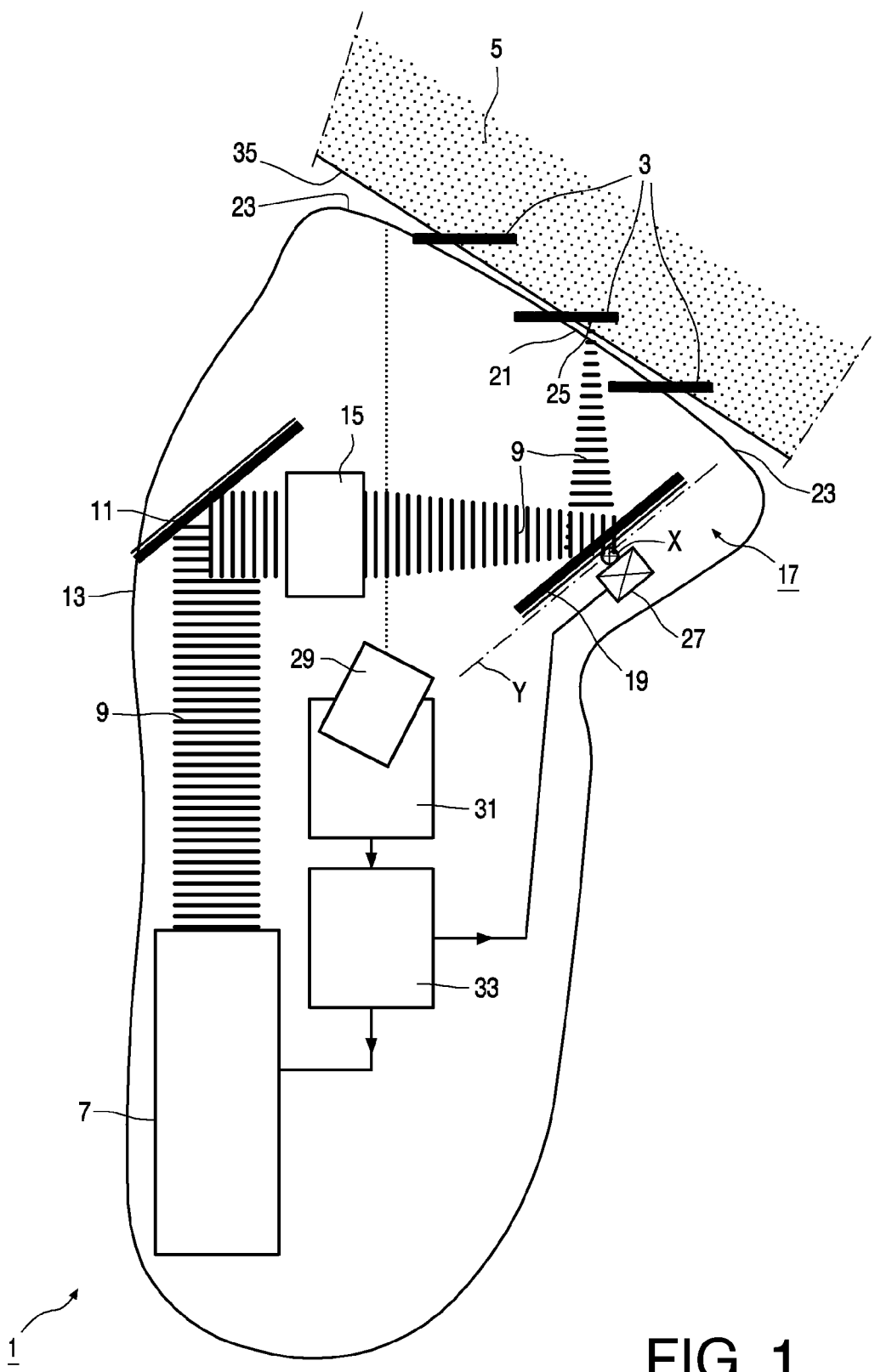

amount of total energy which is necessary to cause trauma and induce (semi-)permanent cessation of hair-growth is at such a level that irritation and damage of the surrounding skin tissue is very limited or even completely prevented.

16 Claims, 4 Drawing Sheets

(56) References Cited

U.S. PATENT DOCUMENTS

| | | | |
|---|---|---|---|
| 3,834,391 A * | 9/1974 | Block | 606/9 |
| 4,388,924 A | 6/1983 | Weissman | |
| 4,617,926 A * | 10/1986 | Sutton | 606/9 |
| 5,653,706 A * | 8/1997 | Zavislan et al. | 606/9 |
| 5,752,948 A | 5/1998 | Tankovich | |
| 5,984,915 A * | 11/1999 | Loeb et al. | 606/9 |
| 6,358,242 B1 | 3/2002 | Cecchetti | |
| 2002/0173781 A1 * | 11/2002 | Cense et al. | 606/9 |
| 2002/0173782 A1 * | 11/2002 | Cense et al. | 606/9 |

FOREIGN PATENT DOCUMENTS

| | | |
|---|---|---|
| WO | 0062700 | 10/2000 |
| WO | WO 0062700 A1 * | 10/2000 |
| WO | 2005011510 | 2/2005 |

* cited by examiner

HAIR-GROWTH CONTROL DEVICE AND HAIR-GROWTH CONTROL METHOD

The present invention relates to a hair-growth control device comprising a laser beam source for providing a laser beam with a pulse time, a laser beam guiding means, and a control unit for determining a target position for the laser beam.

Document WO00/62700 discloses a device of the kind mentioned in the opening paragraph. In one embodiment of the known device, laser energy is supplied to the root of a hair in order to thereby heat and kill the root as well as the skin tissue present in the immediate vicinity. Hence, the hair-growth is permanently inhibited, or at least for a longer period of time.

A problem of the known device is that it is inefficient, in that a relatively large amount of energy is supplied to the skin. Too much of the supplied energy will be absorbed by untargeted tissue, such as skin tissue above and/or below the root of the hair. In many cases, there is a too high risk that tissue outside the targeted root tissue is affected. This may cause e.g. pain and necrosis of untargeted cells.

It is an object of the present invention to provide a hair-growth control device of the kind mentioned in the opening paragraph that is more energy efficient and safer.

In order to achieve the object of the present invention, a hair-growth control device in accordance with the invention is characterized in that the control unit is able and arranged to determine as the target position a position within a predetermined distance from hair-growth related skin tissue situated between 0.3 and 5 mm below the surface of a skin to be treated when the device is in an operative position on the skin, and the device further comprises an optical focusing system for focusing the laser beam to a focal spot with a power density, wherein the power density in the focal spot is above a local threshold value for inducing a laser induced optical breakdown phenomenon in skin tissue.

Note that for the purpose of the present invention, the expression "skin tissue" is a generic expression, comprising tissues strictly belonging to the skin, such as epidermis, corium etc., but also tissue layers directly below the skin in a strict sense, such as (parts of) hair follicles and capillaries feeding said skin tissue. The same holds for hair-growth related skin tissue. This has been further clarified hereinbelow. Note that the hair tissue, i.e. the club or hair shaft, itself is not comprised in the expressions (hair-growth related) skin tissue.

The target position is specified to a depth between 0.3 and 5 mm below the surface of the skin. This will be further elucidated below.

Furthermore, the optical focusing system allows focusing of the laser beam to a small focal spot. This ensures that the power density outside the focal spot is much lower, and hence the power density of the laser beam before focusing itself can be much lower. This also ensures that hair-growth related tissue outside the focal spot will receive a much lower power density than the focal spot. This increases the selectivity and safety of the device and use thereof. Furthermore, the power density in the focal spot, as determined by the power density in the original laser beam, the dimensions of the focal spot and properties of the skin, is such that a so-called laser induced optical breakdown (LIOB) phenomenon occurs in the hair-growth related tissue.

In general, LIOB occurs in media when the power density of the laser beam in the focal spot exceeds a threshold value, which is characteristic of the particular medium. Below the threshold value, the particular medium has relatively low linear absorption properties for the particular wavelength of the laser beam. Above the threshold value, the medium has strongly non-linear absorption properties for the wavelength, which are the result of ionization of the medium and the formation of plasma, e.g. due to multi-photon absorption. The LIOB phenomenon results in a number of mechanical effects, such as cavitation and the generation of shock waves, which damage the medium (skin tissue) in positions surrounding the position of the LIOB phenomenon.

The LIOB phenomenon has also been mentioned in document WO2005/011510, which relates to a device for shortening hairs, i.e. a shaving device. The device focuses a laser beam in a hair. Even though the document discloses that the hair may be broken e.g. 0.1 mm below the skin surface, it is still a device that shaves without providing long-lasting or permanent effects on hair growth. In fact, the focus position is exclusively in the hair and the pulse energy is limited, in order to prevent that skin tissue surrounding the hair is affected. Hence, long-lasting or permanent effects cannot be obtained with this device. It is also noted that the target group for shaving and epilation is different. For example, a male's bearded skin is not often epilated, while a woman's skin is preferably not shaved but epilated.

It is noted that LIOB, and thus use of the device and method according to the present invention, is not dependent on skin type or hair type. Many prior art methods rely on linear absorption of light by melanin or other pigments. Such methods lead to difficulties e.g. in dark skins or with pale hairs. Contrarily, LIOB according to the present invention relies on non-linear absorption, and is independent of skin type and hair type. In fact, the present device and method may be used for fair skin as well as dark skin, dark hairs and even colorless vellum hairs.

Hair tissue and skin tissue are transparent or semi-transparent to wavelengths between approximately 500 nm and 2000 nm. The linear absorption of the tissues, as well as scattering, is low enough for LIOB to be possible. In particular, the wavelength of the laserbeam is between 800 nm and 1400 nm. For wavelengths within this range, the linear absorption properties and scattering properties are at a minimum, so that a maximum portion of the energy of the generated laser beam is used to cause the LIOB phenomenon in the focal spot of the laser beam, while in surrounding tissue only very small portions of the (scattered) energy is absorbed.

Further details relating to LIOB may be found in the introductory part of the above-mentioned document. Suffice it here to state that the threshold value of the power density is dependent on the pulse time. For example, for a pulse time of 10 ns, the threshold value is about $8*10^{11}$ W/cm$^2$, although some references in literature disclose lower values in this case, such as about $2*10^{10}$ W/cm$^2$. Such values may be readily obtained with even a low energy laser. Note that shorter pulse times, such as in the order of pico seconds or femto seconds are also effective, contrary to the minimum pulse time of 1 ms as required in WO00/62700. Note also that the laser need not have a fixed or predetermined pulse time. A variable pulse time is also possible.

It is noted that the required power density is defined in terms of the result to be achieved; in particular the laser beam and focusing system should generate a power density in the focal spot that is above the LIOB threshold value. However, with knowledge of said threshold value, which is either obtained by theory or by experiments, the skilled person will readily select the laser power and the optical system in order to achieve the required power density.

As mentioned above, the LIOB phenomenon causes a number of mechanical effects, which propagate through the skin tissue, and which traumatize or kill hair-growth related tissue in and around the target position. Obviously, the distance over which such traumatization or cell death occurs is dependent on the pulse energy. For example, with an effective pulse energy absorbed in the plasma of a few tenths of a mJ, cell traumatization may be achieved up to a distance of say 20-50 micrometer, also dependent on the type of hair-growth related tissue and its susceptibility. Note that here, as in the entire present document unless indicated otherwise, the pulse energy indicated relates to the energy that is coupled into, or absorbed by, the plasma in the focal spot. The total energy in the pulse needed to supply such effective energy is larger, depending on scattering, reflection, absorption, et cetera, and may be readily obtained through experiment or sufficiently exact knowledge of the properties of the skin.

In a particular embodiment, the laser beam guiding means comprise an adjustable laser beam manipulator, for example one or more moveable mirrors or other optical elements. Such a manipulator may be employed to position the laser beam on various target positions without having to move the device as a whole. For example trained persons may thus select targets without having to move the device across the skin.

In an alternative embodiment of the device according to the invention, the laser beam guiding means comprise an optical waveguide that is suitable for insertion into a hair follicle, and arranged for guiding the laser beam to an exit opening of the waveguide. In this embodiment, the point-and-shoot principle may still be used, but it is also possible to employ its special features that ensure a treatment of hair-growth related skin tissue. In particular, the laser beam is coupled into the waveguide, and leaves the waveguide through an exit surface. The device allows insertion into the hair follicle, and positioning the device such that the focal spot of the laser beam exiting the optical waveguide is effective in causing a LIOB phenomenon in or sufficiently near to hair-growth related tissue. Since substantially all hair-growth related skin tissue is present in or very near the hair follicle, functionality of the device is easily ensured.

In a special embodiment, the device of the present invention further comprises an image sensor for detecting an image of at least a portion of the skin, wherein the control unit is arranged to determine the target position from the detected image. This allows the device to be used more easily, in that the target position may be determined by the use of an image sensor and a control unit.

The image sensor may provide an image of the skin. The control unit may be arranged for determining a target position from the detected image. This may be performed on the basis of e.g. suitable hair recognition software, which is known per se in the state of the art. Other devices, systems and methods for determining the target position may also be applied, such as manually determining said target position by a trained person.

The above embodiment allows e.g. more easy automation of the device. In particular, the control unit may be operatively coupled to the adjustable laser beam manipulator, such that the control unit is arranged to position the focus on the target position as determined by the control unit. This embodiment allows the user to place the device on a skin to be treated, such that the control unit determines the target position and targets the target position with the laser beam. Such an embodiment is sometimes referred to as a 'point-and-shoot' device.

In a special embodiment, the predetermined distance is at most 50 micrometer. As mentioned above, the distance over which the LIOB induced mechanical effects traumatize and/or kill hair-growth related tissue is dependent on the pulse energy. However, by selecting the pulse energy such that the predetermined distance is at most 50 micrometer, the total energy is such that untargeted tissue is affected hardly at all. In other words, if the distance between the actual focal spot and the target position is at most 50 micrometer, the selectivity and the total supplied pulse energy are satisfactory. Of course, other values may be selected, such as about 30 μm, or 60 μm. Preferably, the predetermined distance is substantially zero. In other words, the focal position and the target position substantially coincide. In other words, the hair-growth related skin tissue is targeted directly.

In a special embodiment, the hair-growth related skin tissue comprises hair follicle tissue and/or blood vessels feeding said follicle tissue. By targeting one or more of the mentioned structures, the growth process of the hair is affected in such a way that the hair-growth is slowed down, stopped and the hair is shed and/or hair-regrowth may be permanently inhibited. The effect may be semi-permanent or permanent, depending on the tissue type that is targeted.

In an advantageous embodiment, the follicle tissue comprises at least one of a matrix, a dermal papilla, a hair bulb, an outer root sheath and stem cells of the hair follicle. The mentioned tissues are parts of the hair follicle that may be affected to influence the hair-growth. E.g., the matrix consists of fast growing tissue that is more sensitive to damaging effects. Once damage is induced in the matrix (apoptosis or necrosis of the cells), the anagen follicle (growth phase) changes to a catagen-like phase, followed by the telogen phase (rest phase) combined with early shedding of the hair. This results in long-lasting, (semi-) permanent hair-growth reduction. The stem cells reside in the so-called bulge region of the follicle. When the stem cells are damaged, the growth cycle is disturbed and hair regrowth may be permanently inhibited.

It is also possible to disturb the mechanical bond between the club of the hair and the follicle. The hair remains loose in the skin, and will fall out or can be removed in any desired way.

Other structures as mentioned above may also be targeted. In particular, blood vessels that feed the hair follicle may be targeted. Targeting these blood vessels can results in cessation of blood flow at the level of the dermal papilla, to stop or slow down hair growth.

It is noted that many of the above-mentioned structures have dimensions, which are substantially smaller than the diameter of a hair. Whereas a hair has a diameter of approximately 0.1 mm, the mentioned structures and tissue have dimensions of about 20-50 micrometer, such as a capillary having a diameter of about 20 micrometer. This ensures that effective damage can be inflicted with a low energy pulse.

In a special embodiment, the image sensor comprises an ultrasound imaging system or an infrared imaging system. Such an image sensor may be used to detect an image of the skin, which has sufficient resolution to determine the location of the skin tissue to be targeted. In general, to be able to locally damage parts of the follicle or blood vessels, an imaging method is useful to determine the location of the target structure. This imaging method is preferably able to penetrate the skin at least down to the level of the target structure (e.g. stem cells or matrix). A method to determine the location of the matrix based on the use of ultrasound is e.g. described in "Sonography of the skin at 100 MHz Enables in Vivo Visualization of Stratum Corneum and Viable Epidermis in Palmar Skin and Psoriatic Plaques", El Gammal et al., Vol 113, Nr. 5, 821-829 (1999). Other known imaging techniques may also be used. Determining the position of the skin tissue to be targeted may also occur indirectly, by locating more easily discernable structures. For example, the bulge region may be located by means of locating the sebaceous gland, and the location of the outer root sheath can be derived from the hair fiber, as there is a concentric layer of tissue around the hair fiber.

Note that the hair-growth related skin tissue is present between about 0.3 and 5 mm below the skin surface. Its depth is somewhat dependent on the hair-type, the growth phase of the hair follicle and, of course, the particular anatomical area. For example, blood vessels are present at a depth of up to 5 mm, and the follicle matrix at between about 2 and 4 mm. Note that this depth is substantially larger than the depth of 0.1 mm disclosed in WO2005/011510. At this depth, the energy in the focal spot is actually smaller than the total pulse energy. This is due to a number of effects, such as reflection at the skin surface, absorption and diffuse scattering in the skin tissue between the skin surface and the focal spot. Based on known skin characteristics, the required pulse energy may be easily determined. For example, for a wavelength of about 1 µm, if a net energy of 0.2 mJ is required at a depth of 2.3 mm, the actually applied pulse energy should be about 2 mJ. The other 1.8 mJ are either reflected, absorbed or scattered in the skin. The intensity and energy are too low to inflict damage outside the focal spot/LIOB region.

The optical system may be preset at a specific depth, e.g. 5 mm, for targeting specific skin types such as capillaries. Advantageously, the optical system has an adjustable focus depth, and is preferably coupled to the control unit. The control unit may select the focus depth based on the determined target position.

The device may comprise adjustment means for positioning the focal spot in the skin. These adjustment means, such as a moveable mirror, may be coupled to the control unit. The control unit may adjust the position of the focal spot on the basis of the position of the hair-growth related tissue to be targeted as detected by the image sensor and determined by the control unit.

The above devices relate in particular to so-called point-and-shoot devices. Such devices may be positioned on the skin, and the imaging system may determine a target position. The device or an operator then positions the laser beam such that the focal spot hits the target spot, or is positioned sufficiently near the target spot for the LIOB phenomenon to have the desired effect. This is either done by an experienced user or automatically, by an automated device, and by means of the laser beam manipulator. An automated device is particularly, though not exclusively, suitable for the consumer market or for use at positions on the skin with large numbers of hairs to be treated.

In an alternative embodiment of the device already mentioned above, the laser beam guiding means comprise an optical waveguide that is suitable for insertion into a hair follicle, and arranged for guiding the laser beam to an exit opening of the waveguide. A device of this type may be used e.g. by an experienced user, such as a dermatologist, or personnel of a beauty parlor. The device has the advantage that it is much simpler than the embodiments mentioned hereinabove, and thus cheaper, more robust etc. The device is preferably but not exclusively used to treat skin with only relatively few hairs, or to treat deviant hairs, etc. Note that many, if not all, of the features of embodiments discussed above may also be combined with this embodiment, such as inclusion of an imaging system etc. Particular features relating to the alternative embodiment are discussed below.

The optical waveguide comprises, in a preferred embodiment, an optical fiber, in particular a mono-mode fiber. An optical fiber may be made sufficiently thin to allow insertion into a follicle. Alternatively, hollow and internally mirrored waveguides etc., are also possible. Such waveguides are often very flexible, which offers easy handling.

Furthermore, use of a waveguide offers decoupling of the actual source of the laser beam and the part of the device actually contacting the skin. This decoupling ensures that the dimensions and the weight of the part of the device contacting the skin may be limited to a minimum for even easier handling.

The optical focusing system preferably comprises either a separate lens or a comparable optical element positioned in front of the exit surface, or alternatively the optical focusing system comprises the exit surface or fiber tip itself, which has been shaped to provide focusing of the exiting laser beam. In particular, the exit surface comprises at least a part that has been shaped into a lens-like form, such as a spherical surface. Thus, the laser beam will exit the waveguide as a focused beam.

In a special embodiment, the device comprises positioning means, arranged for limiting the depth at which the device may be inserted into a follicle. Such a depth may be limited in dependence on the desired target tissue, such as the matrix of the follicle etc., of the type of hair, of the anatomical region of the body and so on. The positioning means may comprise e.g. a projection or protrusion on the waveguide of any kind, at a predetermined distance from the focal spot, and hence in practice at a predetermined distance from the exit surface of the waveguide. In an advantageous embodiment, the positioning means are adaptable in that they allow selecting the distance between the projection or protrusion and the exit surface of the waveguide. In this way the device may be adapted to different types of target tissue, different hair types etc.

In a second aspect of the invention, a method of hair-growth control is provided, which comprises generating a laser beam during a pulse time, focusing said laser beam to a focal spot in skin tissue, within a predetermined distance from a target position in hair-growth related skin tissue relating to a hair of the skin wherein the power density in the focal spot is, for the pulse time, above a local threshold value for inducing a laser induced optical breakdown phenomenon in skin tissue at the focal position. In particular, the effects caused by the LIOB phenomenon, such as mechanical effects and/or direct plasma effects, should then be sufficient to cause the desired effect on the hair-growth related skin tissue at the target position. All of this has already been discussed above.

This method claim, as well as the claims dependent thereon, is substantially the method counterparts of the device claims mentioned above, or relate to a use of the device. Hence, for brevity's sake, the method claims will not all be elucidated in much detail.

In particular, however, the total pulse energy delivered to the hair-growth related skin tissue of each hair is less than about 1 mJ, preferably less than about 0.5 mJ. By providing such a small amount of energy, the risk of unwanted side effects is minimized. The presently claimed method still ensures a good efficacy, since by effectively targeting the focal spot, a long-lasting effect is achieved. Use is made of the fact that said hair-growth related skin tissue has dimensions which are much smaller than the diameter of a hair. For example, a single 0.2 mJ pulse, which is carefully targeted at e.g. the matrix of a hair follicle, will lead to shedding of the hair and a long-lasting inhibition of hair regrowth. Contrarily, in the method according to WO2005/011510, a substantial number of such pulses is required to break the hair, while no long-lasting effect is obtained.

To obtain a total pulse energy coupled into the plasma in the focal spot of less than 1 mJ, or preferably less than about 0.5 mJ, a total pulse energy delivered at skin surface level should be adapted accordingly, in dependence on the depth of the focal spot etc., as already discussed hereinabove. Note that the total pulse energy delivered to the focal spot substantially corresponds to the total pulse energy delivered to the hair-growth related skin tissue if the predetermined distance between the focal spot and the target position is substantially zero.

In an advantageous embodiment of the method, all the energy delivered to the hair-growth related skin tissue of each hair is delivered with a single pulse. This ensures that a high LIOB efficiency is achieved. It turns out that the mechanical effects, such as shock waves, are less efficient for inflicting damage to hair-growth related tissue if the pulse energy is distributed over a plurality of pulses. For example, in WO2005/011510, the mechanical effect that causes (initial) breaking of the hair depends on the shock waves in the longitudinal direction of the hair. By providing a plurality of separate smaller pulses, the combined effect of the separate shock waves in the longitudinal direction is not a simple addition thereof. In fact, the efficiency of the effect is diminished with respect to the effect of one single pulse of equal total pulse energy. However, the total pulse energy required to break or cut the hair with this method is about 4 mJ. At such a pulse energy level, however, unwanted side effects in the skin tissue surrounding the hair may not always be avoidable. In contrast thereto, the presently claimed method does allow a long-lasting effect to be obtained through shedding of the hair using a single pulse of substantially less energy, such as less than 0.5 mJ. Nevertheless, it is also possible to supply more pulses, e.g. to traumatize a tissue structure that extends beyond the range of the LIOB phenomenon. It is for example possible to traumatize the follicle around the hair shaft by firing several small pulses along the circumference thereof. Alternatively, a grid for firing the pulses may be applied in order to traumatize the hair-growth related tissue structure.

The generating of a laser beam during a pulse time corresponds to supplying at least one pulse. If only one pulse is supplied, the pulse has a duration of said pulse time. If a number of pulses are supplied, the total duration of the pulses corresponds to said pulse time.

The present method may be automated by using skin imaging and suitable hair recognition software. The hair recognition software may not only recognize hairs, but preferably also follicle substructures, such as a bulge region and/or a matrix region.

The device according to the invention is very well suited for private use by inexperienced consumers. The laser energy is very low, and there are little or no side effects to the untargeted skin tissue.

Figure 2:
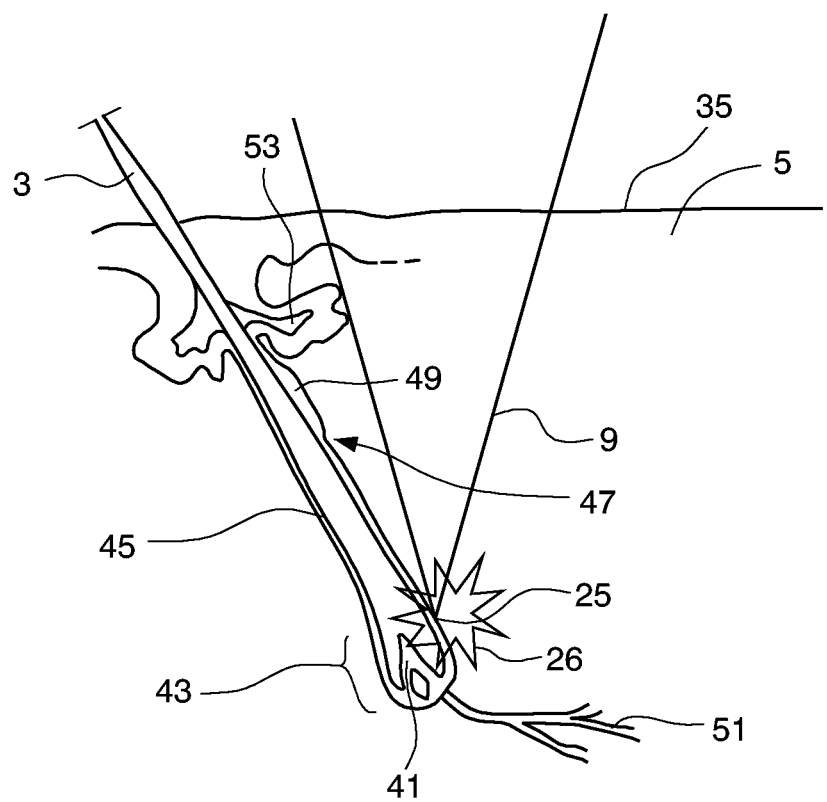
Figure 3:
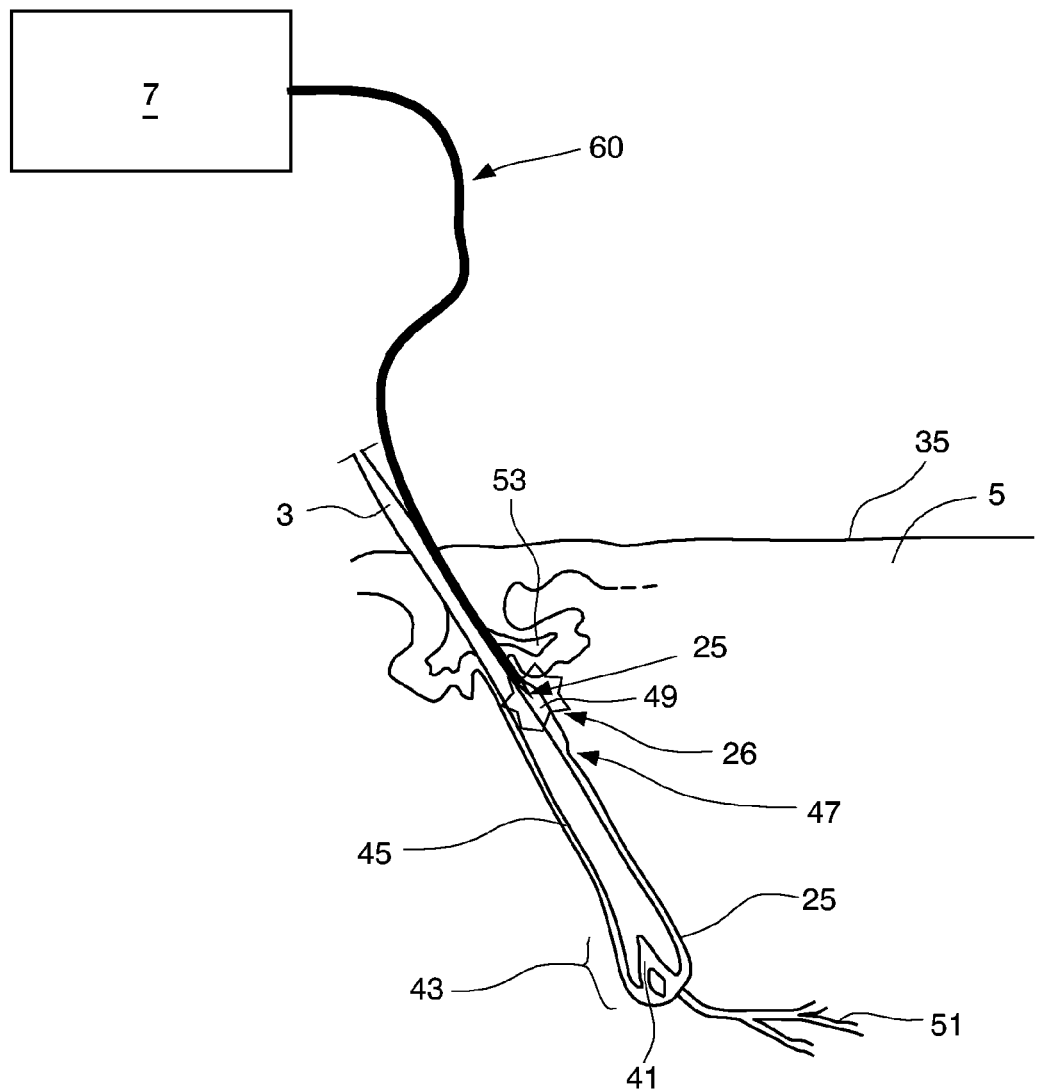
Figure 4:
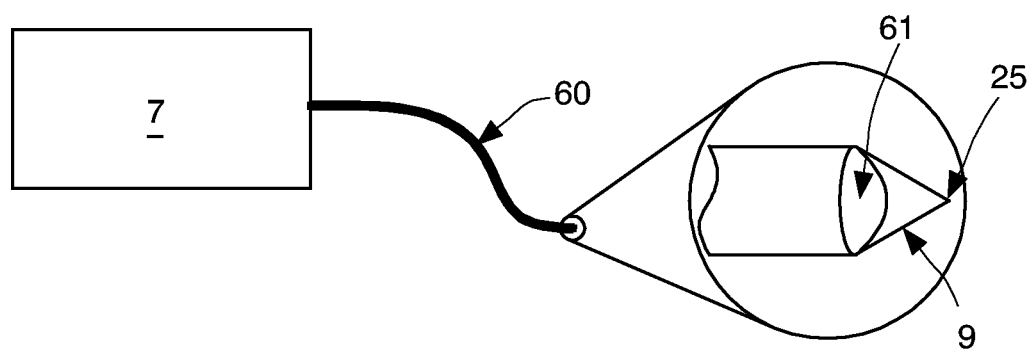

The present invention will now be elucidated further and preferred embodiments thereof will be described in detail with reference to the appended drawings. Therein:

FIG. 1 diagrammatically shows a hair-growth control device in accordance with the invention, FIG. 2 shows in detail a target position of a focal spot of a laser beam of the device of FIG. 1 in a section of skin to be treated, FIG. 3 shows an alternative embodiment of the device, in use, and FIG. 4 diagrammatically shows the device of FIG. 3 with details.

In FIG. 1, only the main components of a device 1 for control of the growth of hairs 3 growing from human skin 5 are schematically shown. The device 1 comprises a laser source 7 for generating a laser beam 9 during a pulse time. In the embodiment shown, the laser source 7 is a pulsed Nd:YAG laser and the generated laser beam 9 has a wavelength of 1064 nm. The generated laser beam 9 follows an optical path from the laser source 7 towards the skin 5 via a first mirror 11, which is mounted in a fixed position in a housing 13 of the device 1, an optical system 15 comprising a lens system or objective, a laser beam manipulator 17 comprising a second mirror 19, and a radiation exit window 21, which is provided in a skin contact surface 23 of the housing 13. The optical system 15 focuses the laser beam 9 to a focal spot 25. The laser beam manipulator 17 comprises an electrical driving member 27, which is only schematically shown in FIG. 1 and by means of which the second mirror 19 is pivotable about a first pivot axis X, which extends parallel to a surface of the second mirror 19 and parallel to the skin contact surface 23, and about a second pivot axis Y, which extends parallel to the surface of the second mirror 19 and perpendicularly to the first pivot axis X. By means of pivotal motions of the second mirror 19 about the first and the second pivot axes X and Y, the focal spot 25 is positioned by the laser beam manipulator 17 in a target position, which is determined in a manner described in the following.

As schematically shown in FIG. 1, the device 1 further comprises an image sensor 29 which is mounted in a fixed position in the housing 13 for detecting an image of at least a portion of the skin 5 with the hairs 3. In the embodiment shown, the image sensor 29 is an ultrasound system. The device 1 further comprises an image recognition system 31 for determining a position and/or orientation of the hairs 3 or surrounding skin tissue structures relative to the skin 5 or hairs 3 on the basis of an image of the skin 5 generated by the image sensor 29. The target position of the focal spot 25 is determined by a control system 33 of the device 1 on the basis of the position and/or orientation of parts of the hairs 3 relative to the skin 5 as determined by the image recognition system 31. A detailed description of the operation of the image recognition system 31 and the control system 33 is omitted here for the sake of simplicity. However, reference is made to the article by El Gammal et al. The article describes a similar image recognition system. On the basis of said description, the person skilled in the art will be able to design and adapt the image recognition system 31 and the control system 33 so as to be suitable for their purposes in the device 1. When the target position has been determined, the control system 33 adjusts the driving member 27 of the laser beam manipulator 17 and, consequently, the second mirror 19 into a position which corresponds to the target position. Subsequently, the control system 33 activates the laser source 7. As in this manner the target position of the focal spot 25 of the laser beam 9 is automatically determined by the control system 33, and the control system 33 automatically activates the laser source 7 after having adjusted the position of the laser beam manipulator 17, the device 1 is particularly suitable for use by non-professional persons, i.e. is particularly suitable for the consumer market.

FIG. 2 shows in detail a target position of a focal spot of a laser beam of the device of FIG. 1 in a section of skin to be treated. It also shows a number of hair-growth related tissue types. Similar structures have been denoted by the same reference numerals.

In particular, a first type of hair-growth related tissue is the matrix 41, which is present in the bulb 43 of the hair. Other types are the outer root sheath 45, stem cells 49 which are present in the bulge region 47, and blood vessels 51 of the hair follicle. Other tissue types, such as the dermal papilla have not been indicated.

The position of the various hair-growth related skin tissue types may be determined by known methods, such as ultrasound or infrared detection. Herein, use may be made of positioning more easily discernable structures, such as the sebaceous gland 53 and the hair fiber 3.

As schematically shown in FIG. 2, in the embodiment shown the control system 33 determines the target position of the focal spot 25 of the laser beam 9 in such a manner that the focal spot 25 is present in or near a portion of the hair-growth related skin tissue which is present at a distance below the skin surface 35. In the embodiment shown, said distance is approximately 0.3-5 mm, depending on e.g. the anatomical area on the body. According to the invention, a dimension of the focal spot 25 and a power of the laser beam 9 generated by the laser source 7 are such that, in the focal spot 25, the laser beam 9 has a power density which is above a characteristic threshold value for skin tissue above which, for the pulse time of the laser beam 9, a laser induced optical breakdown (LIOB) phenomenon occurs in the skin tissue at the location of the focal spot 25. Said LIOB phenomenon is used to e.g. mechanically traumatize the hair-growth related skin tissue, as will be further described in the following.

Focusing of the laser beam 9 to the focal spot 25 causes a LIOB phenomenon, which in turn causes mechanical effects such as a shock wave, schematically indicated by reference numeral 26. These mechanical effects may cause trauma of local or nearby tissue. In the embodiment shown in FIG. 2, the focal spot is aimed at the outer root sheath 45, very near the matrix 41. Locating this target position is relatively easy, since it is at the tissue immediately around the hair fiber, at the end thereof. Applying an effective (local) laser pulse of a few tenths of a mJ, say 0.2 mJ, results in damage to the matrix (bulb), which in turn may cause cessation of hair growth. Of course, aiming at other tissues such as capillaries 49, will also result in (semi)permanent effects on hair regrowth.

In general, the LIOB phenomenon occurs in a medium, which is transparent or semi-transparent to the wavelength of a laser beam when the power density of the laser beam exceeds a threshold value, which is characteristic of the particular medium. Below the threshold value, the medium has a relatively small linear absorption coefficient for the particular wavelength of the laser beam. Above the threshold value, the medium has a strongly non-linear absorption coefficient for the particular wavelength of the laser beam, which is the result of ionization of the medium and the formation of plasma. The LIOB phenomenon results in a number of mechanical effects, such as cavitation and the generation of shock waves, which damage the medium in positions surrounding the position of the LIOB phenomenon. This threshold effect also ensures that absorption outside the focal spot, e.g. due to scattering, is only linear absorption, which is small for the selected wavelength. Since, in addition, outside the focal spot the intensity is much smaller than in the focal spot, undesired side effects, if present at all, are minimal.

Since the laser beam 9 is focused to the focal spot 25, the power density of the laser beam 9 will have a maximum value in the focal spot 25. As a result, when the power of the laser beam 9 is gradually increased, an LIOB phenomenon will first occur in the focal spot 25. The dimension of the focal spot 25 and the power of the laser beam 9 are such that the LIOB phenomenon substantially only occurs in the focal spot 25. In the embodiment of the device 1 according to the invention, the wavelength of the laser source 7 (1064 nm) is a wavelength at which both the hair tissue and the skin tissue present between the skin surface 35 and the focal spot 25 are semi-transparent. As a result, absorption and scattering of the laser beam 9 by the hair tissue and the skin tissue present between the skin surface 35 and the focal spot 25 will be relatively small, so that a relatively large portion of the energy of the generated laser beam 9 is used to effect the LIOB phenomenon in the focal spot 25 and hardly any irritation of the skin tissue and damage of the hair tissue present between the skin surface 35 and the focal spot 25 will occur. It is noted that, in general, the skin tissue present between the skin surface 35 and the intended position of the focal spot is semi-transparent to wavelengths in the range between approximately 800 nm and 1400 nm. As a consequence, embodiments of the present device in positions below the skin surface 35 should preferably have a laser source with a wavelength within said range. Preferably, the wavelength is in the range between approximately 1000 nm and 1100 nm, as in the embodiment of FIG. 1, since for wavelengths within said range the linear absorption and scattering properties of the hair tissue and the skin tissue immediately below the skin surface 35 are at a minimum.

Experiments have shown that the above-described mechanical and other effects, which result from the LIOB phenomenon in the focal spot 25, can lead to trauma or damage to the hair-growth related skin tissue in an area immediately surrounding the focal spot 25. In order to achieve an LIOB phenomenon in the focal spot 25, the power density of the laser beam 9 in the focal spot 25 should be above the characteristic threshold value for skin tissue, as mentioned before. It is noted that said characteristic threshold value for skin tissue is rather close to the threshold value, which is characteristic of the occurrence of LIOB phenomena in aqueous media and aqueous tissue. Furthermore, said characteristic threshold value is dependent on the value of the wavelength of the laser source 7. Furthermore, some scientists believe that the threshold value (W/cm2) decreases when the pulse time increases. In any case, the skilled person will be able to determine said threshold value by means of experiments.

Experiments have further shown that, in order to achieve that the mechanical effects resulting from the LIOB phenomenon are sufficiently strong to cause significant damage of the hair-growth related skin tissue in or near the focal spot 25, a pulse time of the laser source 7 in the order of, for example, 10 ns suffices. In the embodiment of the device 1 shown in FIG. 1, the Nd: YAG laser source 7 has a pulse time of 8 ns. For a value of the pulse time in the order of 10 ns, and a wavelength of 1064 nm, the threshold value of the power density of the laser beam 9 in the focal spot 25 is in the order of $8*10^{11}$ W/cm$^2$. Note that it is rather difficult to actually measure this local intensity. It is however relatively easier to set a laser system such that a LIOB phenomenon actually occurs in the focal spot, whatever its local intensity. The LIOB itself may be actually measured or inferred, and it is thus possible for the skilled person to set the laser system to a desired setting.

Although this threshold value is enormous, it can be readily achieved for the described pulse time with a sufficiently small size of the focal spot 25 and with a total pulse energy of no more than a few tenths of a mJ. The required size of the focal spot 25 is in the order of 10 μm, which is substantially smaller than the average diameter of a hair (100 μm), and can be realized by means of a sufficiently large numerical aperture of the lens system or objective of the optical system 15. In view of said small amount of total pulse energy, irritation and damage of the skin tissue surrounding the target area are limited to an acceptable level or even substantially completely prevented. An advantage of the device 1 in accordance with the invention is that the device 1 provides optimum smoothness of the skin 5, which is maintained for a long time, or even permanently.

From the foregoing description it is clear that local damage in or near the focal spot 25 can be achieved with a single pulse of the laser beam 9, e.g. with a pulse time in the order of 10 ns, having a total amount of pulse energy of no more than a few tenths of a mJ. However, it is also possible to supply more than one pulse, preferably but not exclusively in a grid of different positions. This may for example be used to traumatize cells, which are difficult to localize by means of an imaging method, such as is presently the case for stem cells. Firing in the neighborhood ensures that these cells are traumatized. An advantage of several small pulses over one large pulse is that the skin as a whole is damaged less.

It is noted that local damage of the tissue by means of an LIOB phenomenon in or near the focal spot 25 can also be achieved by means of laser pulses having a pulse time which is considerably smaller than the example of 8 ns in the embodiment described before. Provided that the laser pulses have sufficient pulse energy, pulse times in the order of pico seconds ($10^{-12}$ s) or femto seconds ($10^{-15}$ s) are also effective to cause local damage.

It is further noted that the invention also covers embodiments in which the device has another kind of optical system for focusing the laser beam to a focal spot. Instead of a lens system or objective, for example, a curved mirror may be used. The optical system may for example comprise a beam expander followed by the lens system or objective, which will result in a further reduction of the focal spot size. It is noted that the position of the focal spot 25 in a direction perpendicular to the exit window 21 and the skin surface 35 is determined by the optical properties of the optical system 15 and by the position of the optical system 15 in the optical path between the laser source 7 and the exit window 21. It is noted that a device in accordance with the invention may be additionally provided with an actuator for adjusting said position of the optical system 15 or with a device for adjusting the optical properties of the optical system 15, so that the position of the focal spot 25 in said direction perpendicular to the skin surface 35 may be manually or automatically adjusted. It is finally noted that the invention also covers embodiments in which the laser beam manipulator and/or the laser source are not automatically controlled by a control system 33, but are to be operated and controlled by a professional operator of the device.

FIG. 3 shows an alternative embodiment of the device, in use. Again, similar parts or structures are indicated by the same reference numerals.

Here, the device comprises a laser beam source 7 and an optical fiber 60, that has been inserted into the follicle of a hair 3.

The tip of the fiber, i.e. its exit surface, has been positioned such that the focal spot 25 causes a LIOB plasma, indicated by 26, such that the stem cells 49 are traumatized. For this purpose, the fiber 60 is inserted into the follicle down to a certain depth. The desired depth may be determined with the help of other structures which are more easily recognized, such as the sebaceous gland 53. It is also possible to fix this depth by means of a projection (not shown) fixed to the fiber 60. Alternatively, it is also possible to use the device without any imaging performed by the operator. Since the fiber is inserted into the follicle, and the surrounding outer root sheath is also a targetable hair-growth related skin tissue, further imaging or operator control is not strictly necessary.

FIG. 4 diagrammatically shows the device of FIG. 3 with details.

The laser source 7 is optically coupled to the fiber 60. The fiber 60 has an exit surface 61 that is shaped to have a focusing effect on the laser beam 9, which has a focal spot 25.

The flexible fiber 60 allows great freedom of working to the operator, who only has to handle the fiber. The laser source 7 may be fixedly positioned, or at least be separate from the fiber 60. Hence, it is now possible to use a larger or heavier laser source 7 without affecting the maneuverability of the device as a whole. This offers the possibility of using more types of laser, or a device having a single laser source but a plurality of fibers, each with a separate shutter or other beam control device.

The invention has been described and elucidated by means of exemplary embodiments, which are deemed to be non-limiting.

The invention claimed is:

1. A hair-growth control device, comprising:
   a laser beam source for providing a laser beam with a pulse time,
   a laser beam guiding means,
   a control unit for automatically determining a target position and focus depth for the laser beam,
   wherein the control unit is arranged to determine as the target position a position within a predetermined distance from hair-growth related skin tissue, which is situated between 0.3 and 5 mm below the surface of a skin to be treated when the device is in an operative position on the skin, and
   an optical focusing system for focusing the laser beam to a focal spot with a power density, wherein the power density in the focal spot is above a local threshold value of the corresponding tissue for inducing a laser induced optical breakdown phenomenon in skin tissue.

2. The device of claim 1, wherein the laser beam guiding means comprises an adjustable laser beam manipulator.

3. The device of claim 1, wherein the laser beam guiding means comprises an optical waveguide that is suitable for insertion into a hair follicle, and arranged for guiding the laser beam to an exit opening of the waveguide.

4. The device of claim 1, further comprising an image sensor for detecting an image of at least a portion of the skin, wherein the control unit is arranged to determine the target position from the detected image.

5. The device of claim 1, wherein the predetermined distance is less than or equal to 50 μm.

6. The device of claim 1, wherein the hair-growth related skin tissue comprises hair follicle tissue and/or blood vessels feeding said follicle tissue.

7. The device of claim 6, wherein the follicle tissue comprises at least one of a matrix, a dermal papilla, a hair bulb, an outer root sheath and stem cells of the hair follicle.

8. The device of claim 4, wherein the image sensor comprises an ultrasound imaging system or an infrared imaging system.

9. A method of hair-growth control, comprising:
generating a laser beam during a pulse time,
determining a target position and focus depth for the laser beam,
focusing said laser beam to a focal spot in skin tissue corresponding to the target position and focus depth, within a predetermined distance from a target in hair-growth related skin tissue relating to a hair of the skin,
wherein the power density in the focal spot is, for the pulse time, above a local threshold value of the corresponding tissue for inducing a laser induced optical breakdown phenomenon in skin tissue at the focal spot,
wherein the target position and focus depth are automatically determined by a control unit.

10. The method of claim 9, wherein said predetermined distance is substantially zero.

11. The method of claim 9, wherein the hair-growth related skin tissue comprises hair follicle tissue and/or blood vessels feeding said follicle tissue.

12. The method of claim 11, wherein the follicle tissue comprises at least one of a matrix, a dermal papilla, a hair bulb, an outer root sheath and stem cells of the hair follicle.

13. The method of claim 9, wherein a total pulse energy delivered to the focal spot is less than 1 mJ.

14. The method of claim 9, wherein all the energy delivered to the hair-growth related skin tissue of each hair is delivered with a single pulse.

15. The method of claim 9, wherein a total pulse energy delivered to the focal spot is less than 0.5 mJ.

16. The method of claim 9, wherein a total pulse energy delivered to the focal spot is 0.2 mJ.

* * * * *